(12) United States Patent
Kolditz et al.

(10) Patent No.: US 9,770,019 B2
(45) Date of Patent: *Sep. 26, 2017

(54) KIT FOR PRODUCING FOAMS CONTAINING BISPYRIDINIUM ALKANE

(71) Applicant: L'AIR LIQUIDE, SOCIETE ANONYME POUR L'ETUDE ET L'EXPLOITATION DES PROCEDES GEORGES CLAUDE, Paris (FR)

(72) Inventors: Petra Kolditz, Hamburg (DE); Sabine Behrends, Appen (DE); Anja Behrendt, Hamburg (DE); Andreas Dettmann, Hamburg (DE); Thomas Spuida, Hamburg (DE)

(73) Assignee: L'AIR LIQUIDE, SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,008

(22) Filed: Nov. 18, 2014

(65) Prior Publication Data

US 2015/0141469 A1  May 21, 2015

(30) Foreign Application Priority Data

Nov. 20, 2013 (DE) .................. 10 2013 223 657

(51) Int. Cl.

| A01N 25/16 | (2006.01) |
|---|---|
| A01N 43/40 | (2006.01) |
| A47K 5/14 | (2006.01) |
| A61K 8/44 | (2006.01) |
| A61K 8/49 | (2006.01) |
| A61Q 17/00 | (2006.01) |
| A61K 9/00 | (2006.01) |
| A61K 9/12 | (2006.01) |
| A61K 8/04 | (2006.01) |

(52) U.S. Cl.
CPC ............. *A01N 25/16* (2013.01); *A01N 43/40* (2013.01); *A47K 5/14* (2013.01); *A61K 8/046* (2013.01); *A61K 8/442* (2013.01); *A61K 8/4926* (2013.01); *A61K 9/0014* (2013.01); *A61K 9/12* (2013.01); *A61Q 17/005* (2013.01); *A61K 2800/87* (2013.01)

(58) Field of Classification Search
CPC .......... A01N 25/16; A01N 43/40; A47K 5/14; A61K 8/442; A61K 31/4425; A61K 9/0014; A61K 9/12; A61K 8/046; A61K 8/4926; A61Q 17/005

USPC .......................................... 514/352; 222/190

See application file for complete search history.

(56) References Cited

U.S. PATENT DOCUMENTS

| 4,420,484 A | 12/1983 | Gorman et al. |
|---|---|---|
| 5,354,906 A | 10/1994 | Weitemeyer et al. |
| 6,903,210 B2 | 6/2005 | Behrends et al. |
| 8,105,306 B2 | 1/2012 | Davis et al. |
| 8,841,349 B2 | 9/2014 | Beilfuss et al. |
| 2005/0215461 A1 | 9/2005 | Gluck et al. |
| 2006/0093558 A1* | 5/2006 | Lin et al. .................. 424/47 |
| 2006/0165612 A1* | 7/2006 | Beilfuss et al. ............ 424/49 |
| 2006/0246013 A1* | 11/2006 | Adkins .................. A61K 8/44 424/47 |

FOREIGN PATENT DOCUMENTS

| CA | 1073911 | 3/1980 |
|---|---|---|
| CA | 2 808 263 | 2/2012 |
| DE | 27 08 331 C2 | 9/1977 |
| DE | 196 47 692 A1 | 6/1998 |
| DE | 102005006104 A1 | 8/2006 |
| DE | 103 56 846 A1 | 7/2007 |
| DE | 10 2010 034 819 A1 | 2/2012 |
| EP | 0 560 114 A2 | 9/1993 |
| EP | 1 666 097 A2 | 6/2006 |
| EP | 1669061 A1 | 6/2006 |
| WO | 00/63337 | 10/2000 |
| WO | 2012/069061 | 5/2012 |

OTHER PUBLICATIONS

DE Office Action, dated Oct. 30, 2014, from corresponding DE application.
Rolf Daniels; "The right Galenics for diseased skin."' Pharmazeutische Zeitung edition 24/2009; Aug. 2004, Govi-Verlag, Eschborn, Germany.
O. J. Eigenmann; "Severe anaphylaxis to a new disinfectant: polyhexanide, a chlorhexidine polymer", Schweiz Med Wochenschr 1998; 128:1508-11, Geneva University Hospital, copyright 1998 EMH Schweizerischer Arzteverlag AG and Infomed-Verlags AS.

* cited by examiner

*Primary Examiner* — Robert Cabral
(74) *Attorney, Agent, or Firm* — Young & Thompson

(57) ABSTRACT

A kit for the production of an antimicrobial foam includes: a) a liquid composition which includes a1)one or more bispyridinium alkane and a2)one or more surfactants selected from non-ionic surfactants, amphoteric surfactants and cation-active surfactants, wherein the composition is formulated so that a foam can be produced therefrom, and b) a device for producing the foam from the composition. By using the bispyridinium alkanes the foam stability of liquid and surfactant-containing compositions is increased.

5 Claims, 1 Drawing Sheet

KIT FOR PRODUCING FOAMS CONTAINING BISPYRIDINIUM ALKANE

Figure 1:
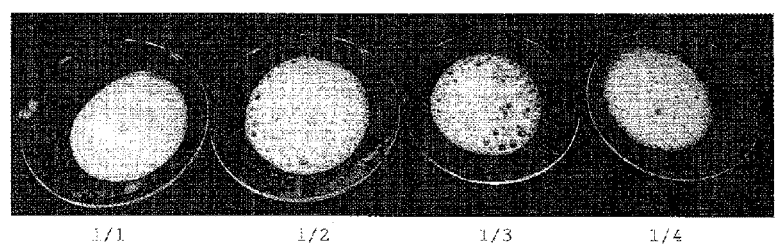

The present invention relates to a kit for producing an antimicrobial foam from a liquid composition. The invention also relates to the use of bispyridinium alkanes for increasing the stability of liquid foams.

The advantages of foams, for example in cosmetic, pharmaceutical and disinfectant applications, are well known. A foam can be distributed more easily than a liquid, wets wounds or hair in some circumstances longer than a liquid, but unlike a semi-solid composition becomes liquid over time and as foam is clearly visible for the user. Furthermore, the haptic properties of foams increase the user compliance. In addition, the general advantages of foams which contain an antimicrobial component are well known (cf. e.g. R. Daniels, Pharmazeutische Zeitung, 24/2009 Govi-Verlag, Eschborn).

WO 2012/069061 A2 discloses a shaving composition for treating pseudofolliculitis of the beard. The composition necessarily contains alkylamidoalkylaminoxide. However, compositions which necessarily contain aminoxide are discussed critically.

EP 1 666 097 A2 discloses a secondary foaming mouthcare foam which is released from a gel. However, gels which are foaming can only wet a limited area and develop the desired properties there.

The product ProntoMan® foot-care foam (Prontomed GmbH, Hiddenhausen, Germany) contains a polyhexanide-betaine complex. However, Olivieri et al describe cases of severe sensitivity to polyhexanide (Schweiz Med Wochenschr 1998; 128:1508-11). Polyhexamethylene biguanide hydrochloride is also under discussion at the European Chemical Agency (ECHA, Helsinki, Finland) because of potential acute toxicity from inhalation and possible carcinogenicity.

The product Stellisept® Med Foam of the company Paul Hartmann AG (Heidenheim, Germany) contains didecyldimonium chloride as the universally used quaternary ammonium compound which is also suitable for surface disinfection. Said quaternary ammonium compound is not typically used however for the disinfection of skin, wounds and mucous membranes.

The product Deb InstantFOAM® of Deb Group Limited (Denby, Great Britain) is an alcohol-based hand disinfectant which is dispensed in the form of foam. However, alcohol-based compositions cause dry skin with repeated use.

To produce a foam that is stable over time surface-active substances (surfactants) are required. However, conventionally used surfactants have the disadvantage of being irritating to the skin above a certain content level and of causing other negative effects on the skin. Larger amounts of surfactant also represent a significant cost factor. Therefore, as little surfactant should be used as possible. To achieve the antimicrobial effect of the foam also an antimicrobial active substance has to be found which—apart from its antimicrobial effect—does not influence the properties of the foam and preferably even improves it.

The underlying objective of the present invention is therefore to provide a composition from which foams can be produced. The composition should be able to be formulated flexibly. Furthermore, the foam should be based on a composition which produces stable foam over a longer time. Said composition should be able to be formulated with a comparatively small amount of surfactant and should have an antimicrobial effect.

It has been found surprisingly that said objectives are achieved by a kit which comprises a) a liquid composition with a content of a1) bispyridinium alkane and a2) special surfactant. The composition a) is thus formulated so that a liquid foam can be produced therefrom. In addition, the kit b) comprises a device for producing the liquid foam from the composition.

In addition, the invention relates to the use of bispyridinium alkanes for increasing the stability of liquid and surfactant-containing foams.

The invention is also based on the fact that it was found that by combining a1) bispyridinium alkanes with a2) selected surfactants liquid foams can be formulated with a reduced content of surfactant, which in addition produce a foam that is stable over time. By means of bispyridinium alkanes compositions for producing liquid foams can be formulated very flexibly. In addition, the bispyridinium alkanes have an antimicrobial effect, which is why the presence of further antimicrobial active ingredients is not absolutely necessary in the compositions according to the invention.

Thus in a first embodiment the invention relates to a kit for the production of an antimicrobial foam comprising:
a) a liquid composition which comprises a1) one or more bispyridinium alkanes and a2) one or more surfactants selected from non-ionic surfactants, amphoteric surfactants and cation-active surfactants, the composition being formulated so that a foam can be produced therefrom and
b) a device for producing the foam from the composition.

In a preferred embodiment the kit consists of composition a) and device b).

According to the invention liquid foams are produced (unlike the teaching of DE 10 2010 034 819 A1 for example which relates to (polyurethane) foams).

a1) Bispyridinium Alkane

The term bispyridinium alkane includes here the bis-[4-substituted-amino)-1-pyridinium] alkanes of the general formulae (I) or (II) disclosed in DE 27 08 331 C2

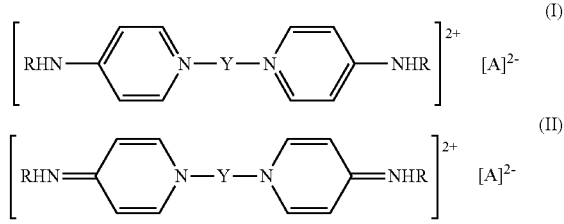

wherein
Y is an alkylene group with 4 to 18 carbon atoms,
R is an alkyl group with 6 to 18 carbon atoms or a cycloalkyl group with 5 to 7 carbon atoms or the phenyl remainder which is substituted by a halogen atom and
A is an anion or a plurality of anions.

The above definition for A applies strictly to monovalent and bivalent anions, A can of course also be a polyvalent anion, e.g. phosphate to orthosilicate. Furthermore, the term bispyridinium alkane includes the different prototropes of compounds of formula (I), as is disclosed for example in DE 196 47 692 A1.

In all of the embodiments of the invention however it is preferred that the bispyridinium alkane is octenidine dihydrochloride (R=n-octyl, Y=n-decenyl; A=2×Cl, hereinafter referred to as "octenidine"). Component a1) is thus particularly preferably octenidine dihydrochloride.

Preferred amounts of component a1) in the composition a) used according to the invention are 0.005 to 1.0 wt. %, preferably 0.01 to 0.5 wt. %, more preferably 0.03 to 0.3 wt. %, even more preferably 0.04 to 0.2 wt. %, such as 0.05 to 0.15 wt. %, for example about 0.08 wt. %, relative respectively to the total weight of composition a).

a2) Surfactant

As component a2) the compositions according to the invention contain one or more surfactants selected from non-ionic surfactants, amphoteric surfactants and cation-active surfactants.

A typical amount of component a2) is 0.01 to 10 wt. %, in particular 0.03 to 2 wt. %, in particular 0.05 to 1 wt. %, such as 0.1 wt. %, relative to the weight of composition a).

As surfactant a2) amphoteric surfactants are particularly preferred, in particular betaines are preferred. Suitable betaines are described for example in EP 560 114 A2. Cocamidopropyl betaine is particularly preferred. Component a2) is thus particularly preferably cocamidopropyl betaine.

Examples of amphoteric surfactants are capryl/capramidopropyl betaine (e.g. Tego Betain 810), sodium cocoamphoacetate (e.g. Rewoteric Am C), cocamidopropyl betaine (e.g. Tego Betain F50), sodium cocoamphopropionate (e.g. Rewoteric AM KSF), disodium cocoamphodiacetate (e.g. Rewoteric AM 2C NM), undecylenamidopropyl betaine (e.g. Rewoteric AM BU 185), cocamidopropyl betaine/glyceryl laurate (e.g. Tego Betain HS KE5), lauryl hydroxysultaine (e.g. Betadet S-20), cocamidopropyl hydroxysultaine (e.g. Crodateric CAS 50-LQ-(MH), disodium cocoamphodiacetate (e.g. Betadet THC-2), disodium cocoamphodipropionate (e.g. Amphoterge K-2N) and coamidopropyl hydroxysultaine (e.g. Betadet SHR).

A preferred amount of amphoteric surfactant a2), such as betaine, in particular cocamidopropyl betaine, is 0.01 to 10 wt. %, more preferably 0.02 to 2 wt. %, in particular 0.03 to 0.5 wt. %, such as 0.04 wt. %, relative to the weight of composition a).

As the non-ionic surfactant all suitable non-ionic surfactants can be used, wherein (i) (fatty)alcohol polyalkoxylates, (ii) sorbitan esters, (iii) alkyl glycosides (in particular alkyl polyglucosides), (iv) aminoxides and (v) ethylene oxide/propylene oxide block copolymers are preferred.

Fatty alcohol alkoxylates, e.g. isodecyl ethoxylates with different proportions of ethylene oxide, isotridecyl ethoxylates, polyethylene glycol ether of stearyl, lauryl and cetyl and oleyl alcohol belong to the (i) alcohol polyalkoxylates. In this case the alcohols can have been alkoxylated by ethylene oxide, propylene oxide or any mixtures of ethylene oxide and propylene oxide. Alcohol polyalkoxylates are known with the names Lutensol®, Marlipal®, Marlox®, Brij® and Plurafac®. Lauryl alcohol ethoxylates are particularly preferred as the non-ionic surfactant.

Furthermore, as the non-ionic surfactants (ii) sorbitan esters are used which are mostly present in the form of oleates, stearates, laurates and palmitates and which are denoted as polysorbates (e.g. Tween®)

Examples of non-ionic surfactants are sucrose cocoate (e.g. Crodesta SL40-LQ, PPG-5-Ceteth-20 (e.g. procetyl aws), Laureth-2 (e.g. Arlypon F), Glycereth-2-cocoate (e.g. Levenol H&B), Glycereth-7-caprylate/caprate (e.g. Emanon EVE) and macrogol hydroxystearate 40 EO).

Furthermore, the non-ionic surfactant can be a (iii) alkyl glycoside, such as an alkyl glucoside (i.e. an alkyl glycoside of glucose), more preferably a $C_8$- to $C_{20}$-alkyl polyglucose, in particular a $C_8$- to $C_{16}$-alkyl polyglucose of a fatty alcohol, wherein a lauryl polyglucose, a decyl polyglucose or a mixture thereof is preferred. The C-chain length in the cocoyl polyglucose is 8 to 16 atoms, in the lauryl polyglucose 12 to 16 C-atoms and in the decyl polyglucose also 8 to 16 C atoms.

A typical amount of alkyl glycoside is 0.03 to 10 wt. %, preferably 0.06 to 5 wt. %, in particular 0.1 to 2 wt. %.

An example of a (iv) aminoxide is cocamidopropyl aminoxide, which is preferred, if in composition a) an aminoxide is included as a2) non-ionic surfactant. However, the composition a) is preferably free of aminoxide.

Cationic surfactants, such as quaternary ammonium salts are also suitable as surfactant a2). In principle, according to the invention all suitable quaternary ammonium compounds can be used. Preferably, the quaternary ammonium compound is a dialkyl dimethyl ammonium salt.

According to the invention advantageously used quaternary ammonium salts are provided using the formula $[R^1R^2R^3(CH_3)N]^+[X]^-$, wherein $R^1$ to $R^3$ can be equal or different and are selected from $C_1$- to $C_{30}$-alkyl, aralkyl, alkenyl and mixed groups, which can comprise one or more atoms selected from O, S, N and P, wherein $R^1$ to $R^3$ are for example $C_8$- to $C_{18}$-alkyl, benzyl or methyl, preferably $C_9$- to $C_{18}$-alkyl, benzyl or methyl, such as $C_{16}$-alkyl, benzyl or methyl. X is an anion (an inorganic or organic acid). In this case both the anion and cation of the quaternary ammonium salt can be polyvalent ions, from which a stoichiometry $[A^{(n+)}]_m[K^{(M+)}]_n$ is produced.

According to the invention all of the quaternary ammonium salts of the above formula known from the prior art are suitable as quaternary ammonium salts, as disclosed for example in WO 00/63337, referred to here. Preferably however, dialkyl dimethyl ammonium salts are used, for example dialkyl dimethyl ammonium chloride, the alkyl chains of which are selected independently from one another from $C_8$- to $C_{18}$-alkyl, preferably $C_9$- to $C_{18}$-alkyl, such as $C_{16}$-alkyl. In the case of dialkyl dimethyl ammonium salts one of the methyl groups can be an alkoxylated, for example ethoxylated, hydromethyl group.

According to the invention preferably used quaternary ammonium salts are compounds of formulae $[R^1N(CH_3)_3]^+$ $[X]^-$, $[R^1R^2N(CH_3)_2]^{+*}[X]^-$ and $[R^1R^2R^3(CH_3)N]^+[X]$, wherein $R^1$ to $R^3$ are selected independently from one another from $C_8$- to $C_{18}$-alkyl and $—(CH_2—CHR^4O)_n—R^5$, wherein n is an integer from 1 to 20, preferably 1 to 5, and $R^4$ and $R^5$ which can be equal or different from one another, H and/or $C_1$- to $C_4$-alkyl are preferably H.

Examples of anions and classes of anions of the used quaternary ammonium salts are hydroxide, sulphate, hydrogen sulphate, methosulphate, ethosulphate, lauryl sulphate, lauryl ether sulphate, cellulose sulphate, sulphamate, halogenide (fluoride, chloride, bromide, iodide), nitrite, nitrate, carbonate, hydrogen carbonate, phosphate, alkyl phosphate, metaphosphate, polyphosphate, thiocyanate, (rhodanide), carboxylic acid salt such as benzoate, lactate, acetate, propionate, citrate, succinate, glutarate, adipate, toluol sulphonate (tosylate) and salicylate. Particularly preferred anions are chloride and propionate.

Examples of cationic surfactants are cetrimonium chloride (e.g. Quartamin 60L or Varisoft 300), behentrimonium chloride (e.g. Quartamin AB, palmitamidopropyltrimonium chloride (e.g. Varisoft PATC), undecylenamidopropyltrimonium methosulphate (e.g. Tetranyl U) and cocotrimonium methosulphate (e.g. Luviquat Mono LS).

Particularly preferably, the quartenary ammonium salts mecetronium ethylsulphate (hexadecyl(ethyl)dimethyl ammonium-ethyl sulphate) and benzalkonium chloride are used.

Additional Components

In addition to a1) bispyridinium alkane as the bifunctional active substance and a2) one or more of the said surfactants the composition contains in a preferred embodiment one or more of the following optional components a3) one or more aliphatic or aromatic alcohols,
a4) one or more solvents and/or
a5) one or more active and or auxiliary substances.

a3) Aromatic Alcohol

By way of example aromatic alcohols are selected from i) aryloxy alkanols, ii) arylalkanols and iii) oligoalkanolarylethers.

According to the invention (i) aryloxy alkanols used have the formula Ar—O—$(CHR)_n$—OH with R=independent H (for n • 2) or $C_1$- to $C_6$-alkyl, wherein n is an integer and is preferably 2 to 10, more preferably 2 to 6 and in particular 2 or 3. Whilst the group Ar can be a core-substituted or unsubstituted aryl group, unsubstituted aryl e.g. phenyl or naphthyl are preferred. Aryloxy alkanols used by way of example according to the invention are phenoxy ethanol and phenoxy propanols. Preferred phenoxy propanols are 1-phenoxypropanol-2,2-phenoxypropanol-1 or mixtures thereof and 3-phenoxypropanol-1. (ii) Aryl alkanols used according to the invention have the formula Ar—$(CHR)_n$—OH with R=independent H or $C_1$- to $C_6$-alkyl, wherein n is an integer and is preferably 1 to 10, more preferably 1 to 6 and in particular 1, 2, 3 or 4. Whilst the group Ar can be a core-substituted or unsubstituted aryl group, unsubstituted aryl, e.g. phenyl or naphthyl, are preferred. By way of example aryl alkanols are 3-phenylpropanol-1, phenethyl alcohol, veratry alcohol(3,4-dimethyoxyphenylmethylalcohol), benzyl alcohol and 2-methyl-1-phenyl-2-propanol.

For example phenoxy-di-, -tri- and -oligoethanol and phenoxy-di-, -tri- and -oligopropanol belong to the (iii) oligoalkanol arylethers.

In this case an embodiment is preferred in which the aromatic alcohol is phenoxyethanol.

A preferred amount of aromatic alcohol (in particular phenoxyethanol) in the composition is 0.1 to 10 wt. %, preferably 0.3 to 8 wt. %, 0.5 to 5 wt. %, in particular 1 to 3 wt. %, such as 2.0 wt. % aromatic alcohol.

Preferably, the composition a) contains less than 10 wt. % aliphatic alcohol, preferably less than 5 wt. %, wherein the composition a) is in particular essentially free of aliphatic alcohol.

a4) Solvent

Furthermore, the liquid composition optionally contains a3) solvent. The preferred solvent is water. The liquid composition is thus in all embodiments of the invention preferably an aqueous composition.

a5) Further Active and/or Auxiliary Substances

Examples of additional active and/or auxiliary substances which can be optionally included in the compositions according to the invention are skincare additives, refatting agents, perfumes, scents, thickening agents, pH regulators, humectants and colorants. The latter include:

polyols, which act as skincare additives, refatting agents and humectants, such as glycerin, erythritol, 1,2,6-hexanetriol, inositol, lactitol, maltitol, mannitol, methylpropanediol, phytantriol, polyglycerol, sorbitol and xylitol, wherein glycerin is particularly preferable, glycerol esters, preferably glycerol cocoate, isopropyl myristate, isopropyl palmitate and triglycerides which act as refatting agents and/or allantoin, urea and aloe vera which function as skin care additives.

Furthermore, in the composition according to the invention one or more glycerolmonoalkyether can be included, as disclosed for example in DE 103 56 846 A1. Particularly preferred is 1-(2-ethylhexyl)glycerol ether (Sensiva® SC50).

The preferred pH values of the composition are in the range of 3 to 9, preferably 4 to 8, such as 4.5 to 7, for example about 5.5. The desired pH can be adjusted for example by lactic acid/sodium lactate, citric acid/citrate or NaOH.

The compositions according to the invention are used in the usual manner on living surfaces, in particular human skin.

Examples of compositions a) for use on living or non-living surfaces are:

skin and hand disinfectants,
surface and instrument disinfectants,
cosmetic products, such as e.g. washing lotions,
pharmaceutical products and
cleaners of all kinds.

The production of the foam of composition a) is performed by a suitable and known technique. The foaming can be performed mechanically or by the addition of suitable propellants and/or by the use of suitable foam dispensers.

In one embodiment preferred compositions contain a6) one or more propellant, preferably air, nitrogen or a mixture of propane with butane or mixtures thereof. The device b) used according to the invention then contains a container in the form of an aerosol bottle.

In this preferred embodiment the composition is thus stored in a pressure container, wherein the pressure container is part of the device and the composition contains a propellant gas, which expands under normal pressure in order to form the foam.

In an alternative embodiment which is particularly preferred the composition is pumped out mechanically by means of a foam dispenser, which is part of the device, wherein the dispenser foams the composition with air. According to this alternative the composition a) thus does not contain a propellant.

In a particularly preferred embodiment the kit comprises:
a) a liquid composition with a content of
  a1) 0.04 to 0.2 wt. %, such as 0.05 to 0.15 wt. %, for example about 0.08 wt. % bispyridinium alkane (preferably octenidine dihydrochloride),
  a2) 0.02 to 2 wt. %, for example 0.03 to 0.5 wt. %, such as about 0.04 wt. % surfactant selected from non-ionic surfactants, amphoteric surfactants and cation-active surfactants (preferably coacmidopropyl betaine),
  and possibly
  a4) water as a solvent and
  a5) glycerin, pH-regulators and skincare products (such as Sensiva SC 50 and allantoin),
  wherein the composition is formulated so that a foam can be produced therefrom and wherein the composition is formulated without propellants, and
b) a device for producing the foam from the composition, wherein the device comprises a foam dispenser, which is provided with air for foaming the composition.

In a second embodiment the invention relates to the use of bispyridinium alkanes to increase the stability of liquid and surfactant-containing foams, and in particular the use of bispyridinium alkanes to increase the stability of liquid foams which contain the aforementioned non-ionic surfactants a2).

Advantages of a foam produced according to the invention are mainly in the composition which makes it possible to omit components and reduce the amount of individual compounds compared to other forms of administration. A foam can be distributed very easily and can thus be used more economically. The user is provided with the following advantages:

- the omission or reduction in the amount of components, in particular the amount of surfactant a2), means fewer disadvantageous effects on a surface, such as e.g. the skin. Such disadvantageous effects can include skin irritation, skin drying, skin degreasing or sensory disadvantages. A foam also makes it possible to save costs and also adhere to legal requirement.
- Furthermore according to the invention the user compliance is improved compared to alternative forms of application. This occurs because exactly the right amount of antimicrobial substance is used that is needed and can be well distributed.
- The foams are stable over time and are also well preserved by the antimicrobial substance. They have reduced formula costs and improved skin tolerance, fewer skin drying and skin degreasing properties than conventional cosmetic or pharmaceutical foams. Furthermore, legal requirements can be adhered to more easily.
- Liquid foam can be spread over the skin unlike solid foam (e.g. wound dressings).
- The amount of surfactant thus does not need to be increased. Instead the amount of surfactant can be reduced with the addition of bispyridinium alkane. Bispyridinium alkanes, such as octenidine dihydrochloride thus have at least two advantageous effects in compositions for foams, namely both an antimicrobial (and thus also self-preserving) effect and a booster effect on the foam formation of conventional surfactants.

The advantages of the invention are also given in the following examples (data in wt. %, unless otherwise indicated).

EXAMPLES

Method—Foam Test
Required Materials
Mixing cylinder, content 100 ml, with graduation and stopper
Stopwatch
Method The solution to be tested is filled into the cylinder up to the 30 ml mark avoiding the formation of foam. The cylinder is then sealed. If foam does form during the filling of the cylinder the test is only carried out once the foam has completely settled.

The cylinder is hit forcefully vertically downwards ten times and the stopwatch is started. Then the total volume of foam and solution is read in milliliters immediately and after 3 minutes.

Formulations were produced in the following manner: the bispyridinium alkane a1) was dissolved in water by stirring and then if necessary the surfactant a2) was added and dissolved by stirring. The amounts of the respective components and results according to the foam test are represented below in Table 1:

TABLE 1

Formulations and results of the foam test

|  | 1 | 2 | 3 | 4 |
|---|---|---|---|---|
| Purified water, % | 99.783 | 99.737 | 99.833 | 99.95 |
| Octenidine dihydrochloride, % | 0.05 | — | — | 0.05 |
| Cocamidopropyl betaine (38%), % | 0.132 | 0.264 | 0.132 | — |
| Active content cocamidopropyl betaine, % | 0.05 | 0.10 | 0.05 | — |
| Total active content, % | 0.10 | 0.10 | 0.05 | 0.05 |
| Foam immediately, ml | 89 | 84 | 80 | 58 |
| Foam after 3 min., ml | 89 | 84 | 80 | 30 (no foam) |

As shown in Table 1, the formulation of example 1 shows an improved foam profile despite cocamidopropyl betaine relative to the formulation of example 2 with a reduced surfactant amount. The total active content (sum of active content of surfactant and active content bispyridinium alkanes) is the same in this case.

The foam is also stabilised over a longer time period despite the reduced surfactant content to a higher level than in example 2.

Example 3 shows with a surfactant concentration similar to example 1 a lower foam profile, both immediately and also after 3 minutes. Example 4 with bispyridinium alkanes alone therefore foams less immediately after producing foam and not at all after 3 minutes.

Therefore, it is all the more surprising that example 1 has a marked foam profile.

It was thus established surprisingly that the surfactant content can be reduced by the addition of bispyridinium alkane whilst maintaining the original active content.

The starting point was the surfactant cocamidopropyl betaine with an active content of 0.1%. This formulation was halved in the active content to 0.05% and replaced by the addition of 0.05% octenidine to the original total active content of 0.1%. The foaming activity of the formulation is virtually identical, even increased, although octenidine itself has hardly any foaming activity.

Figure 2:
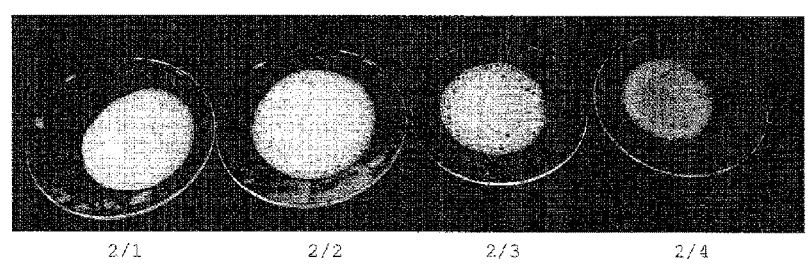

The results of corresponding tests are also shown in FIGS. 1 and 2,

FIG. 1 shows foams produced by the formulations according to table 1 (immediately) and FIG. 2 shows foams produced by the formulations according to table 1 (after 3 minutes).

FIG. 1 shows the foam of example 1 (cf. 1/1, according to the invention), of examples 2 and 3 (1/2 and 1/3, without bispyridinium alkane a1), comparative example) and of example 4 (without non-ionic surfactant a2) comparative example) immediately after the foam has been produced.

Said foams are then shown in FIG. 2 after 3 minutes, wherein the foam of example 4 (2/4, comparison) has completely collapsed, whereas the foam of the formulation according to the invention is still very well defined and stable by comparison (2/1).

The invention claimed is:
1. Kit for the production of an antimicrobial foam consisting of:
   (a) a liquid composition consisting of:
      (a1) 0.04 to 0.2 wt % octenidine dihydrochloride,
      (a2) 0.02 to 2 wt % cocamidopropyl betaine, and
      (a3) water as a solvent,
      wherein the composition is formulated so that a foam can be produced therefrom; and

(b) a foam dispenser for foaming the composition with air.

2. The kit according to claim 1, wherein the octenidine dihydrochloride is present in an amount of 0.05 to 0.15 wt. %.

3. The kit according to claim 1, wherein the cocamidopropyl betaine is present in an amount of 0.03 to 0.5 wt. %.

4. The kit according to claim 1, wherein the octenidine dihydrochloride is present in an amount of about 0.08 wt %.

5. The kit according to claim 1, wherein the cocamidopropyl betaine is present in an amount of about 0.04 wt %.

* * * * *